(12) United States Patent
Ahn et al.

(10) Patent No.: US 9,133,521 B2
(45) Date of Patent: Sep. 15, 2015

(54) COMPOSITION FOR DIAGNOSING ALZHEIMER'S DISEASE USING METHYLATION STATUS OF HMOX1 GENE AND METHOD FOR DIAGNOSING ALZHEIMER'S DISEASE USING THE SAME

(71) Applicant: Ewha University—Industry Collaboration Foundation, Seoul (KR)

(72) Inventors: Jung-Hyuck Ahn, Seoul (KR); Hye-Youn Sung, Seoul (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 121 days.

(21) Appl. No.: 13/870,226

(22) Filed: Apr. 25, 2013

(65) Prior Publication Data

US 2014/0162252 A1      Jun. 12, 2014

(30) Foreign Application Priority Data

Dec. 7, 2012   (KR) .................. 10-2012-0141957

(51) Int. Cl.
*C07H 21/04*   (2006.01)
*C12Q 1/68*    (2006.01)

(52) U.S. Cl.
CPC ........ *C12Q 1/6883* (2013.01); *C12Q 2600/154* (2013.01)

(58) Field of Classification Search
None
See application file for complete search history.

(56) References Cited

U.S. PATENT DOCUMENTS

| 4,666,829 A | 5/1987 | Glenner |
| 5,231,000 A | 7/1993 | Majocha |
| 2003/0148326 A1 | 8/2003 | Olek |
| 2004/0048279 A1 | 3/2004 | Olek |
| 2004/0146946 A1 | 7/2004 | Perry |
| 2009/0117589 A1 | 5/2009 | Southern |
| 2010/0203520 A1 | 8/2010 | Liew |

FOREIGN PATENT DOCUMENTS

| WO | 89-06242 | 7/1989 |
| WO | 92-17152 | 10/1992 |
| WO | 01-26536 | 4/2001 |

OTHER PUBLICATIONS

Sung et al. (The 20th Federation Meeting of Korean Basic Medical Scientists, Apr. 26-27, 2012, P-036 , see IDS).*
Sung et al. (2012 KSBMB Annual Meeting, May 30-Jun. 1, 2012).*
Sung et al. (Society of Free Radical Research International, Sep. 6-9, 2012, Imperial College, London UK, #562).*
Tai et al., "A rapid and inexpensive method for isolation of total DNA from dehydrated plant tissue," Plant Mol. Biol. Reporter, vol. 8(4), p. 297-303 (Nov. 1990).
Murray et al., "Rapid isolation of high molecular weight plant DNA," Nucleic Acids Research, vol. 8, No. 19, p. 4321-4325 (Oct. 1980).
Hye Youn Sung et al., "Amyloid Protein-Mediated Differential DNA Methylation Status Regulates HMOX1 Expression in Alzheimer's Disease Model," The 20th Federation Meeting of Korean Basic Medical Scientists (Apr. 26, 2012).
Hye Youn Sung et al., "Epigenetic Regulation of HMOX1in Alzheimer's disease," 2012 Korean Society Biochemistry and Molecular Biology Annual Meeting (May 30, 2012).
H.Y. Sung et al., "Amyloid protein-mediated epigenetic changes regulates HMOX1 expression in Alzheimer's Disease model," 16th Biennial Meeting of the Society for Free Radical Research International (Sep. 6, 2012).

* cited by examiner

*Primary Examiner* — Jeanine A Goldberg
(74) *Attorney, Agent, or Firm* — Lex IP Meister PLLC,

(57) ABSTRACT

The present invention relates to a diagnostic composition for Alzheimer's disease which includes an agent measuring the methylation level of HMOX1 gene promoter, a diagnostic kit and a method for diagnosing Alzheimer's disease using the same.

2 Claims, 5 Drawing Sheets

COMPOSITION FOR DIAGNOSING ALZHEIMER'S DISEASE USING METHYLATION STATUS OF HMOX1 GENE AND METHOD FOR DIAGNOSING ALZHEIMER'S DISEASE USING THE SAME

CROSS REFERENCE TO RELATED APPLICATION

This application claims priority to and the benefit of Korean Patent Application No. 10-2012-0141957 filed on Dec. 7, 2012, which is hereby incorporated by reference for all purposes as if fully set forth herein.

BACKGROUND OF THE INVENTION

1. Field of the Invention

The present invention relates to a diagnostic composition for Alzheimer's disease which includes an agent measuring the methylation level of HMOX1 (Heme oxygenase 1) gene promoter, a diagnostic kit and a method for diagnosing Alzheimer's disease using the same.

2. Description of the Related Art

Alzheimer's disease (AD) is a representative degenerative brain disorder that results in degeneration of nerve cells, leading to loss of cognitive ability and memory. It progresses over time and eventually leads to death due to other complications. Alzheimer's disease can occur in people in their forties or fifties, and the incidence of Alzheimer's disease increases with age approaching 40 to 50% at the age of 85 to 90.

As the number of those with Alzheimer's disease is increasing rapidly with the current aging of the population, the need for early diagnosis, prevention and treatment is growing. However, the diagnosis of Alzheimer's disease has been made only by neuropsychological tests (e.g., mini-mental state examination (MMSE)) or specialized MRI scans which require much time and cost.

Other biochemical methods have been also proposed for the diagnosis of Alzheimer's disease, for example, a method for detecting the level of beta amyloid protein or tau protein in the cerebrospinal fluid or serum, a method for detecting glial fibrillary acidic protein (GFAP)-antibody or the like. However, convenience and accuracy of the diagnostic methods are still in doubt (International Patent Publication No. 92/17152; U.S. Pat. No. 4,666,829; International Patent Publication No. 89/06242; U.S. Pat. No. 5,231,000, etc.).

Meanwhile, HMOX1 (Heme oxygenase 1) is a heat shock protein 32 (HSP32) that exists in the endoplasmic reticulum, and it binds with NADPH cytochrome p450 reductase to convert a pro-oxidant heme to CO, $Fe^{2+}$ and biliverdin which is subsequently converted to an antioxidant bilirubin by biliverdin reductase. The conversion of biliverdin to bilirubin contributes to protection of cells from oxidative stress. However, there have been no reports that epigenetic changes in the methylation status of HMOX1 gene promoter can be used for the diagnosis of Alzheimer's disease.

The present inventors have found Alzheimer's disease-specific hypomethylation of HMOX1 gene promoter. They have confirmed that diagnosis of Alzheimer's disease can be made by measuring the methylation level of HMOX1 gene promoter using a biomarker, thereby completing the present invention.

SUMMARY OF THE INVENTION

An object of the present invention is to provide a diagnostic composition for Alzheimer's disease including an agent measuring the methylation level of HMOX1 gene promoter.

Another object of the present invention is to provide a diagnostic kit for Alzheimer's disease including the composition.

Still another object of the present invention is to provide a method for diagnosing Alzheimer's disease by measuring the methylation level of HMOX1 gene promoter.

DETAILED DESCRIPTION OF THE PREFERRED EMBODIMENTS

Based on the finding of Alzheimer's disease-specific hypomethylation of HMOX1 gene promoter, the present invention provides a technique for diagnosing Alzheimer's disease by measuring the methylation level of HMOX1 gene promoter.

In one aspect, the present invention relates to a diagnostic composition for Alzheimer's disease including an agent measuring the methylation level of HMOX1 (Heme oxygenase 1) gene.

As used herein, the term "methylation" refers to attachment of methyl groups to bases constituting genomic DNA. Preferably, the methylation, as used herein, means methylation that occurs at cytosines of specific CpG sites in a particular gene promoter. If methylation occurs, binding of transcription factors is inhibited to suppress expression of a particular gene. If non-methylation or hypomethylation occurs, expression of the particular gene is increased.

As used herein, the phrase "measuring the methylation level" means to determine the methylation level of HMOX1 gene promoter, and the methylation level can be determined by methylation-specific PCR, for example, methylation-specific PCR (methylation-specific polymerase chain reaction, MSP), real time methylation-specific PCR (real time methylation-specific polymerase chain reaction), PCR using a methylation DNA-specific binding protein, and quantitative PCR. Alternatively, it can be determined by automatic sequencing such as pyrosequencing and bisulfite sequencing, but is not limited thereto. A relatively high methylation level of HMOX1 gene promoter is observed in a sample from a person without Alzheimer's disease, whereas specific hypomethylation of HMOX1 gene promoter is observed in a sample from a person with Alzheimer's disease. Thus, diagnosis of Alzheimer's disease can be made by determining the methylation level of the promoter.

Preferably, measurement of the methylation level of HMOX1 gene promoter in the present invention means to measure the methylation level at the CpG site of HMOX1 gene promoter, and more preferably to measure the methylation level of cytosine at the CpG site located at −374 from the transcription start site of HMOX1 gene. The sequence of HMOX1 gene promoter is represented by SEQ ID NO. 1, and the cytosine base at the CpG site located at −374 from the transcription start site of HMOX1 gene corresponds to position 627 of SEQ ID NO. 1, based on SEQ ID NO. 1.

In the genomic DNA of mammal cells, there is the fifth base in addition to A, C, G and T, namely, 5-methylcytosine, in which a methyl group is attached to the fifth carbon of the cytosine ring (5-mC). 5-mC is always attached only to the C of a CG dinucleotide (5'-mCG-3'), which is frequently marked CpG. The methylation of this CpG inhibits a repetitive sequence in genomes, such as alu or transposon, from being expressed. In addition, the 5-mC of this CpG is naturally deaminated to thymine (T), and thus, this CpG is a site where an epigenetic change in mammal cells occurs most often.

As used herein, the term "HMOX1 gene" is a gene encoding Heme oxygenase 1 that exists in the endoplasmic reticulum, and Heme oxygenase 1 binds with NADPH cytochrome p450 reductase to convert a pro-oxidant heme to CO, $Fe^{2+}$ and biliverdin which is subsequently converted to an antioxidant bilirubin by biliverdin reductase. The conversion of biliverdin to bilirubin contributes to protection of cells from oxidative stress. The base sequence of human HMOX1 gene can be identified by Genbank Accession No. NM_002133.2.

The present inventors examined aberrant methylation status of the particular CpG sites of HMOX1 gene promoter in Alzheimer's disease, and its association with clinicopathological features. As a result, they found that Alzheimer's disease can be diagnosed by determining the methylation level of the particular CpG sites of the HMOX1 gene promoter.

Figure 2:
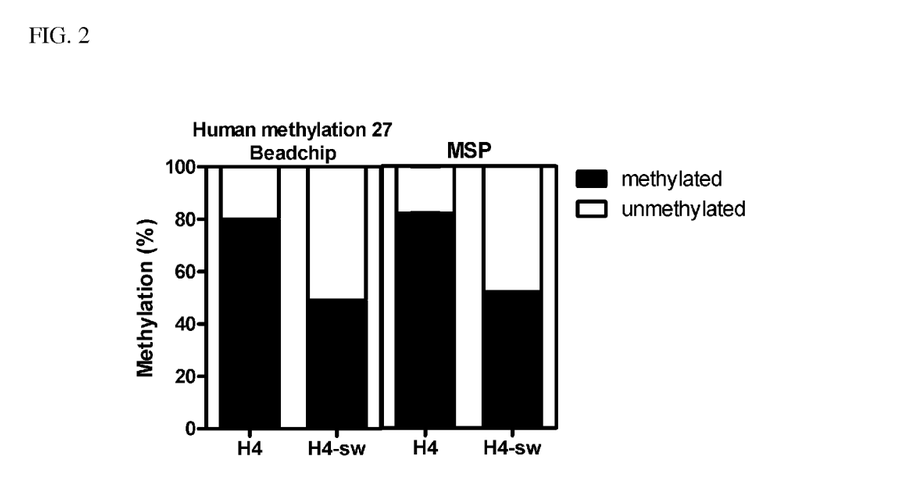
FIG. 2 shows methylation and unmethylation of HMOX1 gene promoter in the Alzheimer's disease model cell line (H4-sw) and normal cell line (H4)
Figure 3:
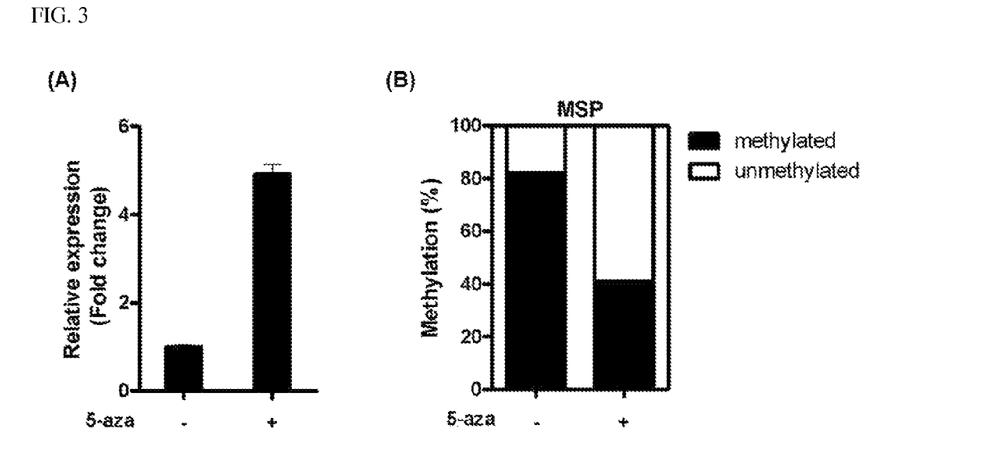
FIG. 3(A) shows HMOX1 expression levels in the normal H4 cell line and 5-aza-2'-deoxycytidin-treated H4 cell line.
FIG. 3(B) shows methylation and unmethylation of HMOX1 gene promoter in the normal H4 cell line and 5-aza-2'-deoxycytidin-treated H4 cell line.

In one specific embodiment of the present invention, the result of methylation array showed that a lower HMOX1 methylation level was observed in an Alzheimer's disease model, APP-swedish mutant-expressing H4 cell line (H4-sw) than in normal cells, and the result of methylation-specific PCR (MSP) also showed similar hypomethylation patterns (FIG. 2). In addition, when a normal H4 cell line was treated with a demethylating agent 5-aza-2'-deoxycytidine, the HMOX1 expression was increased, indicating that HMOX1 expression is regulated by DNA methylation (FIG. 3).

Figure 4:
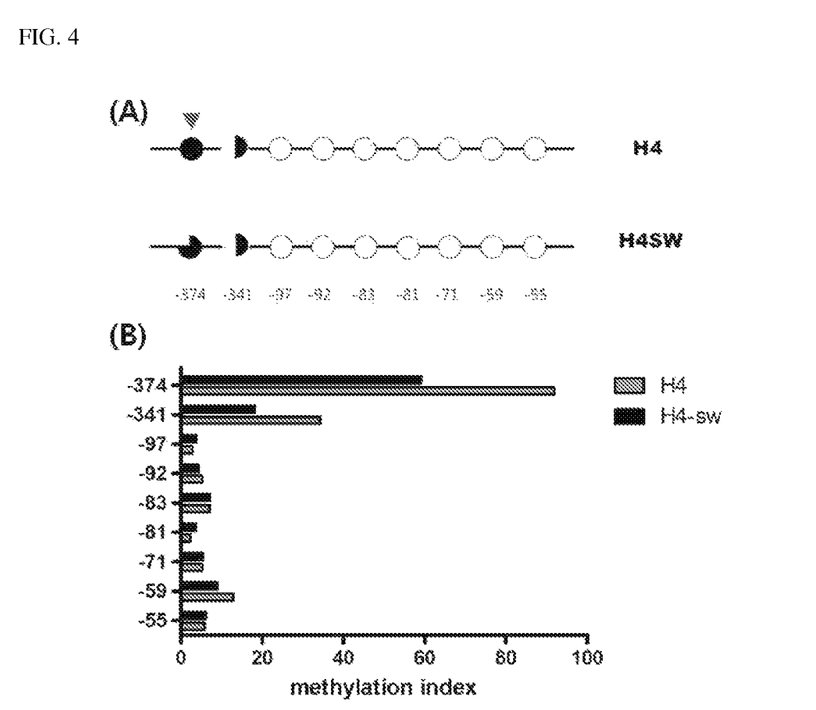
FIG. 4(A) shows methylation status of the promoter CpG sites around 500 bp from the transcription start site in the Alzheimer's disease model cell line (H4-sw) and normal cell line (H4), examined by bisulfite sequencing analysis using bisulfite sequencing PCR (BSP)
FIG. 4(B) shows methylation status of the promoter CpG sites around 500 bp from the transcription start site, examined by bisulfite sequencing using 454 GS-FLX system.
Figure 5:
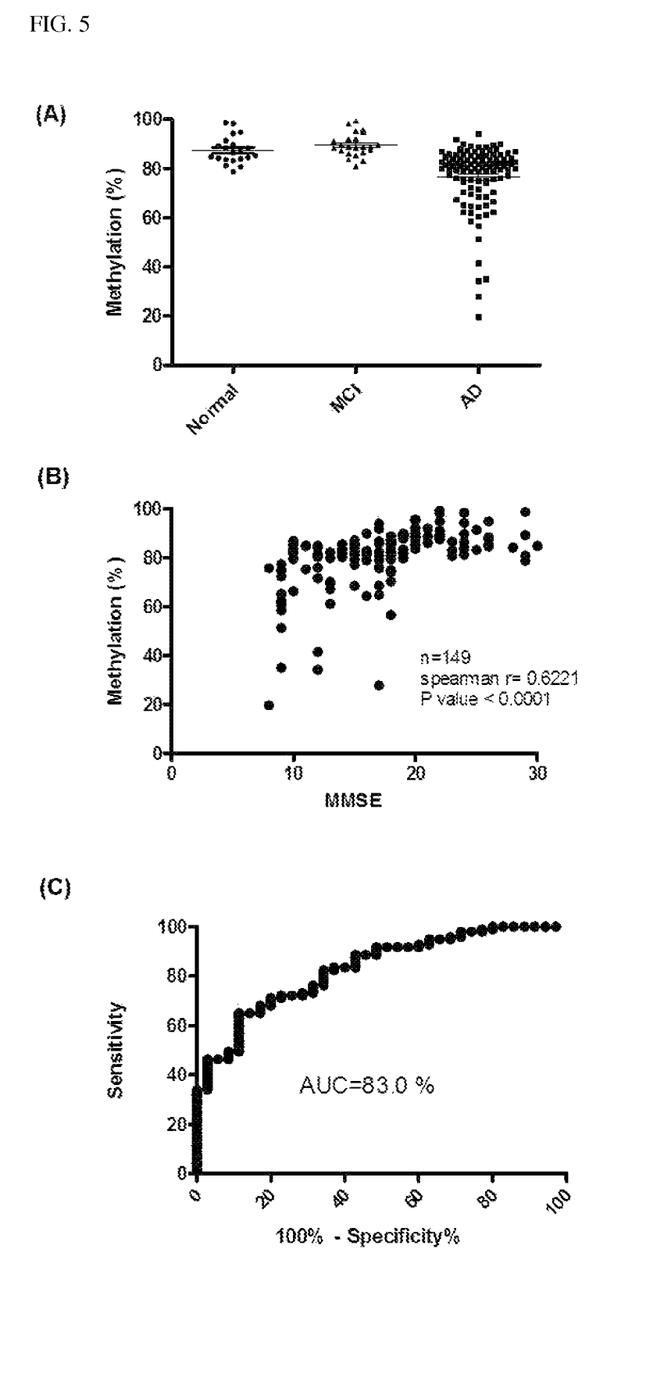
FIG. 5(A) shows comparison of DNA methylation at −374 promoter CpG sites of HMOX1 gene among the blood samples of 105 patients with Alzheimer's disease (AD, aged 80±5.6, MMSE 8-19), 23 patients with mild cognitive impairment (MCI, aged 72.8±5.8, MMSE 20~23) and 21 healthy elderly individuals (Normal, aged 74.5±6.9, MMSE 24 or higher)
FIG. 5(B) shows that there is a close relationship between DNA methylation at −374 promoter CpG sites of the HMOX1 gene and MMSE score.
FIG. 5(C) shows the probability of AD can be predicted by DNA methylation status at −374 promoter CpG sites of HMOX1.

Furthermore, the present inventors found specific hypomethylation of the CpG site located at −374 bp from the transcription start site of HMOX1 gene, compared to normal H4 cell line in bisulfite sequencing analysis (FIG. 4), and also found hypomethylation at HMOX1-374 CpG sites, compared to the control group in the analysis of the blood samples of Alzheimer's disease patients aged 70 or older, suggesting that there is an association between MMSE (mini-mental state examination) of Alzheimer's disease patients and methylation level of −374 CpG sites (FIG. 5). In addition, lower methylation levels were associated with more severe cognitive impairment in Alzheimer's disease patients.

Therefore, it can be seen that the methylation level of the particular promoter region of HMOX1 (the CpG site located at −374 from the RNA transcription start site) can be utilized as a diagnostic biomarker for determining the progression of dementia of Alzheimer's type.

As used herein, the term "diagnosis" refers to evaluation of the presence or properties of pathological states. With respect to the objects of the present invention, the diagnosis is to determine the incidence of Alzheimer's disease, or progression or severity of the disease.

In the present invention, the agent measuring a methylation level of a gene may include a compound modifying an unmethylated cytosine base or a methylation-sensitive restriction enzyme, primers specific to the methylated allele sequence of HMOX1 gene, and primers specific to the unmethylated allele sequence of the gene.

The compound modifying an unmethylated cytosine base may be bisulfite, but is not limited thereto, preferably sodium bisulfite. A method of detecting promoter methylation by modifying the unmethylated cytosine residue using bisulfite is widely known in the art (WO01/26536; US2003/0148326A1).

Further, the methylation-sensitive restriction enzyme is a restriction enzyme capable of specifically detecting CpG methylation, and preferably a restriction enzyme including CG as a restriction enzyme recognition site. Examples thereof include SmaI, SacII, EagI, HpaII, MspI, BssHII, BstUI, NotI or the like, but are not limited thereto. Cleavage by a restriction enzyme differs depending on methylation or unmethylation of C at the restriction enzyme recognition site, and the methylation can be detected by PCR or Southern blot analysis. In addition to the restriction enzymes, other methylation-sensitive restriction enzymes are well known in the art.

The methylation level of the particular CpG site of HMOX1 gene promoter in an individual suspected of having Alzheimer's disease may be determined by obtaining genomic DNA from a biological sample of the individual, treating the obtained DNA with a compound modifying an unmethylated cytosine base or a methylation-sensitive restriction enzyme, amplifying the treated DNA using primers by PCR, and then identifying the presence of the resulting amplified product.

Therefore, the agent of the present invention may include primers specific to the methylated allele sequence of HMOX1 gene, and primers specific to the unmethylated allele sequence of the gene. As used herein, the term "primer" means a short nucleic acid sequence having a free 3' hydroxyl group, which is able to form base-pairing interaction with a complementary template and serves as a starting point for replication of the template strand. A primer is able to initiate DNA synthesis in the presence of a reagent for polymerization (i.e., DNA polymerase or reverse transcriptase) and four different nucleoside triphosphates at suitable buffers and temperature. In addition, the primers are sense and antisense nucleic acids having a sequence of 7 to 50 nucleotides. The primer may have additional properties that do not change the nature of the primer to serve as a starting point for DNA synthesis.

The primers of the present invention can be designed according to the CpG sequence that is subjected to methylation analysis, and may be a set of primers that are able to specifically amplify bisulfite-unmodified cytosine due to methylation and a set of primers that are able to specifically amplify bisulfite-modified cytosine due to unmethylation. Preferably, the primers specific to the methylated sequence of HMOX1 gene may be a set of primers represented by SEQ ID NOs. 10 and 13, and the primers specific to the unmethylated sequence of HMOX1 gene may be a set of primers represented by SEQ ID NOs. 11 and 13.

The diagnostic composition for Alzheimer's disease may further include polymerase, agarose, and a buffer solution for electrophoresis, in addition to the above agent.

In another aspect, the present invention relates to a diagnostic kit for Alzheimer's disease including the composition.

In still another aspect, the present invention relates to a method for diagnosing Alzheimer's disease by measuring the methylation level of the particular CpG site of HMOX1 gene promoter.

In still another aspect, the present invention relates to a method for diagnosing Alzheimer's disease, including the steps of:

(a) measuring a methylation level of HMOX1 (Heme oxygenase 1) gene promoter in a biological sample of an individual, (b) comparing the methylation level to that of the corresponding gene in a control sample without Alzheimer's disease, and (c) determining that the individual has Alzheimer's disease when the methylation level measured in the sample of the individual is lower than that measured in the control sample.

As used herein, the term "biological sample" includes samples displaying a difference in the methylation levels of HMOX1 gene by the incidence of Alzheimer's disease, such as tissues, cells, whole blood, serum, plasma, saliva, sputum, cerebrospinal fluid or urine, but is not limited thereto. Preferably, the biological sample of the present invention may be a tissue.

First, to measure the methylation level of genomic DNAs obtained from the individuals suspected of having Alzheimer's disease, the genomic DNAs can be obtained by a phenol/chloroform extraction method, an SDS extraction method (Tai et al., Plant Mol. Biol. Reporter, 8: 297-303, 1990), a CTAB separation method (Cetyl Trimethyl Ammonium Bromide; Murray et al., Nuc. Res., 4321-4325, 1980) typically used in the art, or using a commercially available DNA extraction kit.

The step of measuring the methylation level of the gene may include the steps of i) treating the obtained genomic DNA in the sample with a compound modifying unmethylated cytosine or a methylation-sensitive restriction enzyme; and ii) amplifying the treated DNA by PCR using primers capable of amplifying the particular CpG site of HMOX1 gene promoter.

In step i), the compound modifying unmethylated cytosine base may be bisulfite, and preferably sodium bisulfite. The method of detecting promoter methylation by modifying unmethylated cytosine residues using bisulfite is widely known in the art.

Further, in step i), the methylation-sensitive restriction enzyme is, as described above, a restriction enzyme capable of specifically detecting the methylation of the particular CpG site, and preferably a restriction enzyme containing CG as a restriction enzyme recognition site. Examples thereof include SmaI, SacII, EagI, HpaII, MspI, BssHII, BstUI, Nod or the like, but are not limited thereto.

In step ii), the amplification may be performed by a typical PCR method. The primers used herein are, as described above, designed according to the particular CpG site that is subjected to methylation analysis, and may be a set of primers that are able to specifically amplify bisulfite-unmodified cytosine due to methylation and a set of primers that are able to specifically amplify bisulfite-modified cytosine due to unmethylation. Preferably, the primers specific to the methylated allele sequence of HMOX1 gene may be a set of primers represented by SEQ ID NOs. 10 and 13, and the primers specific to the unmethylated allele sequence of HMOX1 gene may be a set of primers represented by SEQ ID NOs. 11 and 13.

The step of measuring the methylation level of the particular CpG site of the HMOX1 (Heme oxygenase 1) gene promoter may further include the step of iii) identifying the presence of a product amplified in step ii). In step iii), the presence of the amplified product may be identified by a method known in the art. For example, electrophoresis is performed to detect the presence of a band at the desired size. For example, in the case of using the compound modifying the unmethylated cytosine residues, methylation can be determined according to the presence of the PCR product that is amplified by the two types of primer pairs used in step i), that is, the set of primers that are able to specifically amplify bisulfite-unmodified cytosine due to methylation and a set of primers that are able to specifically amplify bisulfite-modified cytosine due to unmethylation. Preferably, methylation can be determined by treating genomic DNA of a sample with bisulfite, amplifying the CpG site of HMOX1 gene by PCR, and then analyzing the amplified base sequence by bisulfite genomic sequencing.

Further, if a restriction enzyme is used, methylation can be determined by a method known in the art. For example, when the PCR product is present in the restriction enzyme-treated DNA, under the state where the PCR product is present in the mock DNA, it is determined as promoter methylation. When the PCR product is absent in the restriction enzyme-treated DNA, it is determined as promoter unmethylation. Accordingly, the methylation can be determined, which is apparent to those skilled in the art. The term 'mock DNA' refers to a sample DNA isolated from clinical samples with no treatment.

Therefore, the method of providing information for the diagnosis of Alzheimer's disease of the present invention is used to effectively examine the methylation of HMOX1 gene promoter, thereby diagnosing Alzheimer's disease.

Hereinafter, the present invention will be described in detail with reference to Examples. However, these Examples are for illustrative purposes only, and the invention is not intended to be limited thereby.

Example 1

Cell Line and Transgenic Mouse

Human neuroglioblastoma cell line, H4 was cultured in a Dulbecco's modified Eagle medium containing 10% fetal bovine serum, 100 U/mL penicillin, 100 μg/mL streptomycin and 2 mM L-glutamine, and APP695-Swedish mutant (K595N/M596L)-expressing Alzheimer's disease model cell line, H4-sw was cultured in the H4 culture medium supplemented with 500 μg/mL geneticine.

12-month-old APP swe/PS1 transgenic mouse expressing both APP Swedish mutant and exon 9 deletion mutant (B6C3-Tg(APP695)85 Dbo Tg(PSEN1)85 Dbo) was used as an Alzheimer's disease model mouse, and the brain tissues (frontal cortex, hippocampus, cerebellum) were separated from the transgenic mouse and normal littermate mouse to examine changes in the gene expression.

Example 2

Total RNA Extraction

Total RNAs were extracted from the cell line and the brain tissues using an RNeasy mini kit (Qiagen). The extraction method was performed according to the manufacturer's manual. The extracted total RNAs were quantified using a spectrophotometer, and RNA degradation was examined by electrophoresis in a 1% agarose gel.

Example 3

Quantitative Real-Time PCR (qRT-PCR)

For cDNA synthesis, Superscript II reverse transcriptase (Invitrogen) was used. 1 μg of total RNA and 50 ng of oligo dT were denatured at 70° C. for 10 minutes, and then a reaction mixture of 4 μA of 5×RT buffer, 2 μA of 0.1 mM DTT, 4 μA of 2.5 mM dNTP mixture, 200 units of Superscript II reverse transcriptase, 10 units of RNase inhibitor was added thereto. 20 μA of the reaction mixture was reacted at 25° C. for 10 minutes, at 42° C. for 50 minutes, and at 95° C. for 5 minutes for cDNA synthesis. The product was diluted at 1:4, and 2 μA thereof was used as a template of qRT-PCR. For qRT-PCR, 20 μA of a reaction mixture containing 2 μA of cDNA, 10 μl of SYBR Premix EX Taq (Takara Bio), 0.4 μA of Rox reference dye (50× Takara Bio), 200 nM of primer for each gene was reacted using an ABI PRISM 7000 sequence detection system (Applied Biosystems) at 50° C. for 2 minutes and at 95° C. for 10 minutes, and then repeated for 40 cycles (at 95° C. for 15 seconds, and at 60° C. for 1 minute) for amplification. The PCR product was reacted at 95° C. for 15 seconds, at 60° C. for 20 seconds, and at 95° C. for 15 seconds to examine the specificity. GAPDH mRNA expression was used as an internal control, and HMOX1 gene expression was normalized to GAPDH expression level using the $\Delta\Delta C_T$ method. The oligonucleotide primer sequences used were given as follows.

TABLE 1

| | Sequence | SEQ ID NO. |
|---|---|---|
| human HMOX1 (forward) | 5'-GGAACTTTCAGAAGGGCCAG-3' | 2 |
| human HMOX1 (reverse) | 5'-GGAAGTAGACAGGGGCGAAG-3' | 3 |
| human GAPDH (forward) | 5'-AATCCCATCACCATCTTCCA-3' | 4 |
| human GAPDH (reverse) | 5'-TGGACTCCACGACGTACTCA-3' | 5 |
| mouse HMOX1 (forward) | 5'-CACTTCGTCAGAGGCCTGCTA-3' | 6 |
| mouse HMOX1 (reverse) | 5'-GTCTGGGATGAGCTAGTGCTGAT-3' | 7 |
| mouse GAPDH (forward) | 5'-AATGTGTCCGTCGTGGATCT-3' | 8 |
| mouse GAPDH (reverse) | 5'-GGTCCTCAGTGTAGCCCAAG-3' | 9 |

Example 4

Genomic DNA Extraction and DNA Modification Using Bisulfite

Genomic DNAs were isolated from the cell line and whole blood using a QIAamp DNA mini kit (Qiagen). Treatment of the extracted DNA with bisulfite converts cytosine of the DNA bases to uracil. At this time, methylated cytosine is not converted to uracil, and remains as cytosine. Therefore, methylated cytosine can be distinguished from unmethylated cytosine. DNA modification using bisulfite was performed using an EPiTech Bisulfite kit (Qiagen) according to the manufacturer's manual.

Example 5

Quantitative Methylation-Specific PCR (qMSP)

In order to measure the methylation level of the particular CpG sites in HMOX1 gene promoter, genomic DNA was treated with bisulfite, and then each primer was used to distinguish methylated DNA from unmethylated DNA at the particular CpG sites. The primer sequences used were given as follows.

TABLE 2

| | Sequence | SEQ ID NO. |
|---|---|---|
| Methylated HMOX1 (forward) | 5'-TTATTAGGTTATTGTTTTGAGTAGC-3' | 10 |
| unmethylated HMOX1 (forward) | 5'-TTATTAGGTTATTGTTTTGAGTAGT-3' | 11 |
| internal control HMOX1 (forward) | 5'-AGTAGGTGATATTTTAGGGAGT-3' | 12 |
| methylated/ unmethylated/ internal control HMOX1 (reverse) | 5'-TCCCAAAAAATTCCAAAAAACTAAA-3' | 13 |

For qMSP, 20 μl of reaction mixture containing 2 μl (10-100 ng/μl) of bisulfite-treated DNA, 10 μl of SYBR Premix EX Taq (Takara Bio), 0.4 μl of Rox reference dye (50× Takara Bio), and 200 nM of each primer was reacted using an 7500 Fast Real-time PCR system (Applied Biosystems) at 95° C. for 30 seconds, and then repeated for 40 cycles (at 95° C. for 3 seconds, and at 62° C. for 30 seconds) for amplification. The PCR product was reacted at 95° C. for 15 seconds, at 60° C. for 1 minute, and at 95° C. for 15 seconds to examine the specificity. Methylation and unmethylation of the particular CpG sites were normalized using an internal control, and calculated as follows (Ct represents the threshold cycle).

$$\Delta Ct_{meth} = Ct_{meth} - Ct_{internal}$$

$$\Delta Ct_{unmeth} = Ct_{unmeth} - Ct_{internal}$$

$$\text{Percent of methylation} = 100/[1+2^{(\Delta Ct_{meth} - \Delta Ct_{unmeth})}]\%$$

Example 6

Bisulfite Sequencing PCR (BSP)

Genomic DNAs of H4 and H4-sw cell lines were subjected to BSP to explore the CpG sites of HMOX1 gene promoter showing a difference in methylation. Primers capable of amplifying the particular promoter region of HMOX1 (UCSC gene database human GRCh37/hg19, chromosome 22, 35,776,557-35,777,029) were prepared, and used to amplify bisulfite-treated DNAs. The primer sequences used were given as follows.

TABLE 3

|  | Sequence | SEQ ID NO. |
| --- | --- | --- |
| human HMOX1_BSP (forward) | 5'-TAAAGAGGGTGTGAGGAGGT-3' | 14 |
| human HMOX1_BSP (reverse) | 5'-ACAACTAATACCCACTTTCTAA-3' | 15 |

PCR amplification was performed by means of initial thermal denaturation at 95° C. for 5 minutes, followed by 30 cycle of 95° C. for 30 seconds, 55° C. for 30 seconds, and 72° C. for 30 seconds, with a final extension at 72° C. for 5 minutes. The amplified BSP product was electrophoresed in a 1.5% agarose gel, and only the corresponding band was extracted and purified, and then cloned into the yT&A cloning vector (Yeastern Biotech). Methylation of the CpG site of each BSP product inserted in the clone was analyzed using a DNA sequencer.

Example 7

Bisulfite Sequencing Analysis Using 454 GS-FLX System

Construction of single-strand DNA library and emulsion PCR were performed using the purified BSP products, and then sequencing was performed by DNA link Inc. according to a sequencing manufacturer, Roche/454 Life Sciences' method, and sequencing was performed using a GS FLX titanium system (Roche/454 Life Sciences).

Example 8

Treatment of 5-aza-2'-deoxycytidine (5-aza-dC)

H4 cell line was treated with a methylation inhibitor 5-aza-2'-deoxycytidine (Sigma-Aldrich) at a concentration of 10 µM for 3 days, and then inhibition of methylation was examined by MSP, and changes in HMOX1 gene expression were measured by qRT-PCR.

Experimental Results

1. Up-Regulation of HMOX1 Gene in Alzheimer's Disease Model

Figure 1:
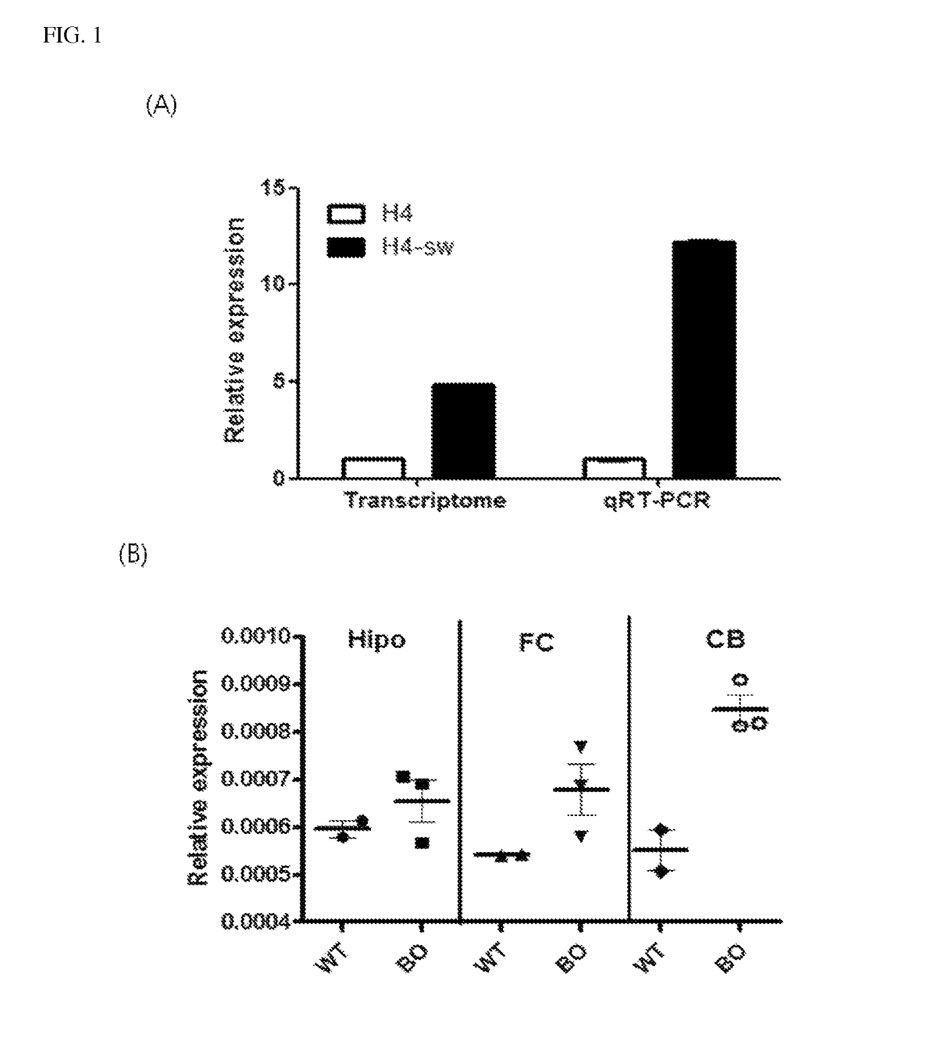
FIG. 1(A) shows HMOX1 expression levels in the Alzheimer's disease model cell line (H4-sw) and normal cell line (H4)
FIG. 1(B) shows HMOX1 expression levels in the brain tissues (Hippocampus, Frontal cortex, cerebellum) of an Alzheimer's disease animal model, APP swe/PS1 transgenic mouse.

The results of transcriptome analysis showed that HMOX1 expression increased by 4.8-fold or higher in the APP-swedish mutant-expressing H4 cell line, compared to the normal cell, and the results of quantitative RT-PCR also showed similar expression patterns (FIG. 1(A)). In addition, increased HMOX1 expression was also observed in the hippocampus, frontal cortex, and cerebellum of the 12-month-old Alzheimer's disease model, APP swe/PS1 transgenic mouse (Borchelt; B6C3-Tg(APP695)85 Dbo/Tg(PSEN1)85 Dbo), compared to the normal mouse (FIG. 1(B)).

2. Regulation of HMOX1 Expression by DNA Methylation

The results of methylation array showed that the methylation level of HMOX1 gene promoter reduced in the APP-swedish mutant-expressing H4 cell line (H4-sw), compared to the normal cell, and the results of methylation-specific PCR (MSP) also showed similar hypomethylation (FIG. 2). When the normal H4 cell line was treated with a demethylating agent 5-aza-2'-deoxycytidin, HMOX1 expression increased (FIG. 3), indicating that HMOX1 expression is regulated by DNA methylation.

3. Identification of Specific CpG Site Playing a Critical Role in HMOX1 Expression Methylation status of the promoter CpG sites around 500 bp from the transcription start site was examined by bisulfite sequencing PCR (BSP) and bisulfite sequencing using 454 GS-FLX system, and the results showed that specific hypomethylation of the CpG site at −374 bp from the transcription start site was found in the H4-sw cell line, compared to the normal H4 cell line (FIG. 4).

4. Close Relationship Between HMOX1 Gene Methylation Status in the Blood of a Patient with Alzheimer's Disease and Cognitive Impairment Genomic DNAs were extracted from 105 patients with Alzheimer's disease (AD, aged 80±5.6, MMSE 8~19), 23 patients with mild cognitive impairment (MCI, aged 72.8±5.8, MMSE 20~23) and 21 healthy elderly individuals (Normal, aged 74.5±6.9, MMSE 24 or higher), and the methylation status of −374 CpG sites of HMOX1 gene was examined. As a result, lower methylation level was observed in patients with Alzheimer's disease than in the control group, and MMSE (mini-mental state examination) score was closely associated with methylation level of −374 CpG sites (FIG. 5). Normal and MCI groups were defined herein as the control group since no significant discrimination was observed between two groups in the methylation level of −374 CpG sites of HMOX1. The ROC analysis revealed good separation of patients with Alzheimer's disease from the control group (AUC=83.0%). In addition, lower methylation levels were associated with more severe cognitive impairment in patients with Alzheimer's disease.

Taken together, it can be seen that the methylation level of the particular promoter region of HMOX1 (the CpG site located at −374 from the RNA transcription start site) can be utilized as a diagnostic biomarker for determining the progression of dementia of Alzheimer's type.

Effect of the Invention

Hypomethylation of the particular CpG site of HMOX1 gene promoter is specific to cells with Alzheimer's disease, and affects HMOX1 expression in a sample of a patient with Alzheimer's disease, and thus Alzheimer's disease can be diagnosed by measuring the methylation level of the HMOX1 gene promoter using a biomarker.

What is claimed is:

1. A method for diagnosing Alzheimer's disease, the method comprising the steps of:

(a) measuring a methylation level of a CpG site located at −374 from a transcription start site of HMOX1 (Heme oxygenase 1) gene in a biological sample of a human individual, the CpG site corresponding to position 627 of SEQ ID NO. 1, (b) comparing the methylation level to a methylation level of a corresponding gene in control samples without Alzheimer's disease, and (c) determining that the human individual has Alzheimer's disease when the methylation level measured in the sample of the human individual is lower than the methylation level measured in the control samples, wherein step (a) comprises the steps of:

treating genomic DNA in the biological sample with bisulfite, amplifying the bisulfite-treated genomic DNA using a set of primers consisting of SEQ ID NOS: 10 and 13, a set of primers consisting of SEQ ID NOS: 11 and 13, or a set of primers consisting of SEQ ID NOS: 14 and 15, and determining the methylation level of the CpG site by a methylation-specific polymerase chain reaction, real time methylation-specific polymerase chain reaction, pyrosequencing, or bisulfite sequencing.

2. The method according to claim 1, wherein the biological sample is tissues, cells, whole blood, serum, plasma, saliva, sputum, cerebrospinal fluid or urine of the human individual.

* * * * *

SEQUENCE LISTING

<160> NUMBER OF SEQ ID NOS: 15

<210> SEQ ID NO 1
<211> LENGTH: 1000
<212> TYPE: DNA
<213> ORGANISM: Homo sapiens
<220> FEATURE:
<221> NAME/KEY: promoter
<222> LOCATION: (1)..(1000)
<223> OTHER INFORMATION: HMOX1_promoter region

<400> SEQUENCE: 1

```
cacagtattg ggaaaggact gtatgaatca tctggtccat tcgttttgtc ctctgggttc      60
acccagtgac cctatttccc ccgagttcta aggagtccac ctcatgcaga attgattcaa     120
taggcgatca gcaagggcca gctctgctct gggccctgag caggcactga gtataagtca     180
gacctgaatg tgcctggaag agtgtcccac gcattccagc agggaagcag tttgtatgac     240
aggtgtccca gtccaggcgg ataccaggtg ctgccagagt gtggaggagg caggcgggga     300
cttagtctcc tccctgggtt tggacactgg catcctgctt tatgtgtgac accactgcac     360
ccctctgagc ctcggtttcc ccatctgtaa aatagaagcg atctaccctc acaggtcagt     420
tgtagggatg aaccatgaaa atactagagt ctctgttttt tgacaggaac tcaaaaaaca     480
gatcctaaat gtacatttaa agagggtgtg aggaggcaag cagtcagcag aggattccag     540
caggtgacat tttagggagc tggagacagc agagcctggg gttgctaagt tcctgatgtt     600
gcccaccagg ctattgctct gagcagcgct gcctcccagc tttctggaac cttctggac      660 gcctggggtg catcaagtcc caaggggaca gggagcagaa gggggggctc tggaaggagc     720
aaaatcacac ccagagcctg cagcttctca gatttcctta aaggttttgt gtgtgtgtgt     780
gtgtgtgtgt gtgtgtgtat gtgtgtgtgt gtgtgtgtgt gtgtgtgttt tctctaaaag     840
tcctatggcc agactttgtt tcccaagggt catatgactg ctcctctcca ccccacactg     900
gcccggggcg ggctgggcgc gggcccctgc gggtgttgca acgcccggcc agaaagtggg     960
catcagctgt tccgcctggc ccacgtgacc cgccgagcat                           1000
```

<210> SEQ ID NO 2
<211> LENGTH: 20
<212> TYPE: DNA
<213> ORGANISM: Artificial Sequence
<220> FEATURE:
<223> OTHER INFORMATION: human HMOX1 primer (forward)

<400> SEQUENCE: 2

```
ggaactttca gaagggccag                                                   20
```

<210> SEQ ID NO 3
<211> LENGTH: 20
<212> TYPE: DNA
<213> ORGANISM: Artificial Sequence
<220> FEATURE:
<223> OTHER INFORMATION: human HMOX1 primer (reverse)

<400> SEQUENCE: 3

```
ggaagtagac agggcgaag                                                    20
```

<210> SEQ ID NO 4
<211> LENGTH: 20
<212> TYPE: DNA
<213> ORGANISM: Artificial Sequence
<220> FEATURE:
<223> OTHER INFORMATION: human GAPDH primer (forward)

<400> SEQUENCE: 4
aatcccatca ccatcttcca                                          20

<210> SEQ ID NO 5
<211> LENGTH: 20
<212> TYPE: DNA
<213> ORGANISM: Artificial Sequence
<220> FEATURE:
<223> OTHER INFORMATION: human GAPDH primer (reverse)

<400> SEQUENCE: 5
tggactccac gacgtactca                                          20

<210> SEQ ID NO 6
<211> LENGTH: 21
<212> TYPE: DNA
<213> ORGANISM: Artificial Sequence
<220> FEATURE:
<223> OTHER INFORMATION: mouse HMOX1 primer (forward)

<400> SEQUENCE: 6
cacttcgtca gaggcctgct a                                        21

<210> SEQ ID NO 7
<211> LENGTH: 23
<212> TYPE: DNA
<213> ORGANISM: Artificial Sequence
<220> FEATURE:
<223> OTHER INFORMATION: mouse HMOX1 primer (reverse)

<400> SEQUENCE: 7
gtctgggatg agctagtgct gat                                      23

<210> SEQ ID NO 8
<211> LENGTH: 20
<212> TYPE: DNA
<213> ORGANISM: Artificial Sequence
<220> FEATURE:
<223> OTHER INFORMATION: mouse GAPDH primer (forward)

<400> SEQUENCE: 8
aatgtgtccg tcgtggatct                                          20

<210> SEQ ID NO 9
<211> LENGTH: 20
<212> TYPE: DNA
<213> ORGANISM: Artificial Sequence
<220> FEATURE:
<223> OTHER INFORMATION: mouse GAPDH primer (reverse)

<400> SEQUENCE: 9
ggtcctcagt gtagcccaag                                          20

<210> SEQ ID NO 10
<211> LENGTH: 25
<212> TYPE: DNA
<213> ORGANISM: Artificial Sequence
<220> FEATURE:
<223> OTHER INFORMATION: Methylated HMOX1 primer (forward)

<400> SEQUENCE: 10
ttattaggtt attgttttga gtagc                                    25

<210> SEQ ID NO 11

```
<211> LENGTH: 25
<212> TYPE: DNA
<213> ORGANISM: Artificial Sequence
<220> FEATURE:
<223> OTHER INFORMATION: unmethylated HMOX1 primer (forward)

<400> SEQUENCE: 11
ttattaggtt attgttttga gtagt                                          25

<210> SEQ ID NO 12
<211> LENGTH: 22
<212> TYPE: DNA
<213> ORGANISM: Artificial Sequence
<220> FEATURE:
<223> OTHER INFORMATION: internal control HMOX1 primer (forward)

<400> SEQUENCE: 12
agtaggtgat attttaggga gt                                             22

<210> SEQ ID NO 13
<211> LENGTH: 25
<212> TYPE: DNA
<213> ORGANISM: Artificial Sequence
<220> FEATURE:
<223> OTHER INFORMATION: methylated/unmethylated/internal control HMOX1
      primer(reverse)

<400> SEQUENCE: 13
tcccaaaaaa ttccaaaaaa ctaaa                                          25

<210> SEQ ID NO 14
<211> LENGTH: 20
<212> TYPE: DNA
<213> ORGANISM: Artificial Sequence
<220> FEATURE:
<223> OTHER INFORMATION: human HMOX1_BSP primer (forward)

<400> SEQUENCE: 14
taaagagggt gtgaggaggt                                                20

<210> SEQ ID NO 15
<211> LENGTH: 22
<212> TYPE: DNA
<213> ORGANISM: Artificial Sequence
<220> FEATURE:
<223> OTHER INFORMATION: human HMOX1_BSP primer (reverse)

<400> SEQUENCE: 15
acaactaata cccactttct aa                                             22
```